United States Patent [19]

Parker et al.

[11] 4,406,282
[45] Sep. 27, 1983

[54] EARPLUG FOR AN UNDERWATER DIVER

[76] Inventors: Bruce W. Parker, 1720 Cinderella Ave.; George L. LeVan, Suite 1200, 500 E. Robinson St., both of Norman, Okla. 73069

[21] Appl. No.: 236,532

[22] Filed: Feb. 20, 1981

[51] Int. Cl.³ ............................................. A61F 11/00
[52] U.S. Cl. ..................................... 128/151; 128/152
[58] Field of Search ................................ 128/151, 152

[56] References Cited

U.S. PATENT DOCUMENTS

| 1,406,425 | 2/1922 | Stair | 128/152 |
|---|---|---|---|
| 2,876,767 | 3/1959 | Wasserman | 128/151 |
| 3,080,011 | 3/1963 | Henderson | 181/23 |
| 3,137,215 | 6/1964 | Taplin | 92/103 |
| 3,259,128 | 7/1966 | Leight | 128/152 |
| 3,373,236 | 3/1968 | Taplin | 264/313 |
| 3,505,999 | 4/1970 | Harvey et al. | 128/152 |
| 3,896,801 | 7/1975 | Gront | 128/152 |
| 3,969,991 | 7/1976 | Comstock et al. | 92/99 |
| 4,060,080 | 11/1977 | Akiyama | 128/152 |
| 4,089,332 | 5/1978 | Rose | 128/152 |

Primary Examiner—Henry J. Recla
Attorney, Agent, or Firm—Robert E. Converse, Jr.

[57] ABSTRACT

An earplug for use by an underwater diver includes a tubular vessel of soft flexible material adapted for insertion into the auditory meatus, a plurality of sealing rings surrounding the vessel to seat against the interior surface of the auditory meatus to provide a watertight seal, and a flexible inner vessel end inwardly rolled back upon itself to define a variable volume between the inner end, the interior surface of the auditory meatus, and the eardrum. The variable volume expands and contracts as the diver ascends or descends to maintain pressure equalization across the eardrum, yet prevent the entry of water into the auditory meatus. If the eardrum should rupture, the inner end of the vessel flexes to its full extent but still prevents the entry of water into the middle and inner ear regions.

11 Claims, 5 Drawing Figures

U.S. Patent    Sep. 27, 1983    4,406,282
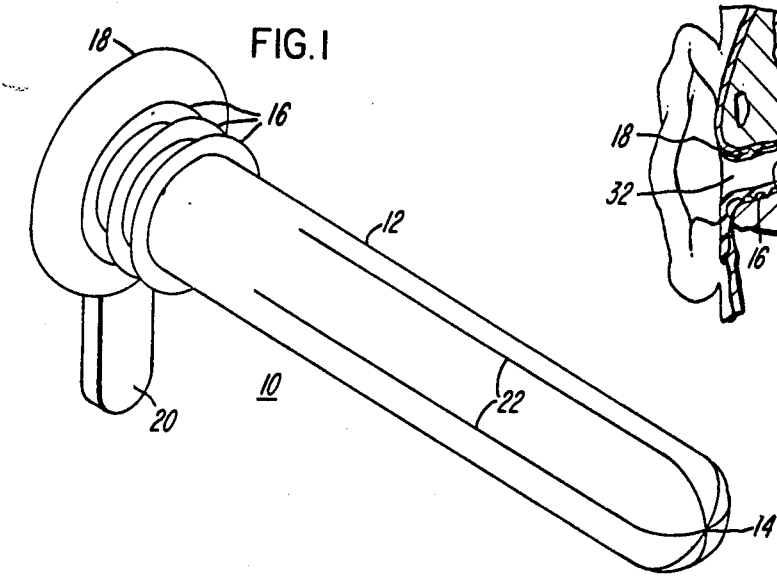
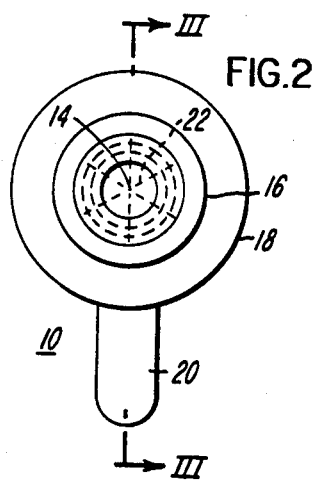
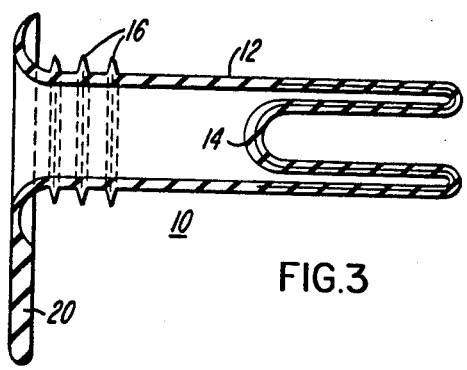
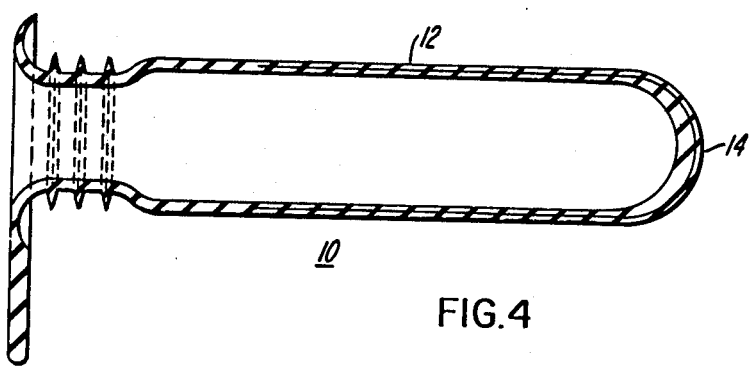

EARPLUG FOR AN UNDERWATER DIVER

BACKGROUND OF THE INVENTION

1. Field of the Invention

The invention is related to earplugs and, more particularly, to earplugs suitable for use by an underwater diver.

2. Description of the Prior Art

Self-contained underwater breathing apparatus (SCUBA) is widely used for military, commercial, and recreational diving. Instead of the heavy sealed diving helmets and clumsy air lines still used for certain diving applications, SCUBA equipment provides greatly increased convenience and freedom of movement. The basic equipment includes one or more tanks of pressurized air, a pressure regulator, and a mouthpiece connected by flexible hose to the regulator and pressurized tank. With the mouthpiece inserted into the mouth of a submerged diver, the regulator provides air, on demand, at the ambient pressure of the surrounding water. Transfer of air at the pressure of the surrounding water through the Eustachian tube allows air pressure in the middle and inner ear regions to balance the water pressure on the outer side of the tympanic membrane, or eardrum. This balancing of pressure on either side of the eardrum is called equalization.

The presence of water in the auditory meatus in direct contact with the eardrum can also introduce dirt, bacteria, and other contaminants to the outer ear region. Furthermore, failure to achieve equalization (due to nasal congestion, equipment failure, or fault of the diver) can result in an inward rupture of the eardrum, permitting the cold water and contaminants to enter the middle and inner ear regions. The immediate problem caused by inundation of these regions is vertigo, the inability to sense up-and-down orientation. This in turn may cause the diver to take irrational action, such as descending to even greater depths or ascending without exhaling, resulting in ruptured lungs. This risk is most likely and most dangerous for the novice diver.

Infection is a serious subsequent problem which can develop from inundation of the inner and middle ear regions with contaminated water. Although such infections are usually treatable, they can cause deafness as well as temporary or permanent inability to dive. In addition to the personal disability of the diver, this can result in serious economic and tactical consequences through loss of manpower resources in commercial and military situations.

Existing earplugs are designed to protect the auditory meatus and eardrum from noise, water, and pressure waves by fixedly sealing the outer end of the auditory meatus. They form a fixed volume of air between the earplug and the eardrum which prevents equalization. The fixed volume of air remains at essentially atmospheric pressure while increasing water pressure during the diver's descent causes a corresponding increase in air pressure in the inner and middle ear regions. The eardrum may eventually rupture in an outward direction.

Although other existing earplugs provide labyrinths or orifices to allow attenuated noise and pressure waves into the auditory meatus, they fail to exclude the entrance of water thereto, and thus give rise to the aforementioned problems of contamination, vertigo, and infection.

It would therefore be desirable to provide an earplug suitable for use in underwater diving, particularly to the depths achievable with SCUBA equipment. This earplug should allow proper pressure equalization during normal conditions and prevent contamination of the auditory meatus and inner and middle ear regions under all conditions, including those resulting from a ruptured eardrum.

SUMMARY OF THE INVENTION

According to a preferred embodiment of the present invention, there is provided an earplug for use by a diver immersed in a surrounding fluid which includes means adapted for insertion into the auditory meatus for establishing a seal around the inner circumference thereof. The earplug further includes means connected to the sealing means for establishing a variable volume further defined by the sealing means, the interior surface of the auditory meatus, and the outer surface of the eardrum. Under normal conditions, variations in pressure of the surrounding fluid cause corresponding pressure variations in the variable volume to allow pressure equalization across the eardrum. Under all conditions, including rupture of the eardrum, surrounding fluid is prevented from penetrating to contact the interior surface of the auditory meatus and the inner and middle ear regions.

BRIEF DESCRIPTION OF THE DRAWINGS

FIG. 1 is a perspective view of an earplug constructed in accordance with the principles of the present invention, showing the earplug in an extended condition;

FIG. 2 is an end view of the earplug of FIG. 1;

FIG. 3 is a sectional view of the earplug of FIGS. 1 and 2, shown in the normal position, taken along line II—II;

FIG. 4 is a sectional view similar to FIG. 3, with the earplug shown in the extended position; and FIG. 5 is a partially schematic view showing the earplug of FIGS. 1 through 4 plugging the external auditory meatus.

DESCRIPTION OF THE PREFERRED EMBODIMENT

Referring now to the drawings, in which corresponding reference characters refer to corresponding members, FIG. 1 shows an earplug 10 constructed in accordance with the principles of the present invention. As can be seen, the earplug 10 includes a tubular bladder or vessel 12 closed at the inner end 14 and constructed of elastomer or other soft flexible elastic material. Integrally molded with the tubular vessel 12 are a plurality of sealing rings 16, an outer sealing flap 18, and a removal tab 20. Optionally, a set of filaments 22 may be molded into the vessel 12 to allow radial expansion and inhibit lengthwise expansion.

Under normal conditions, the closed end 14 of the vessel 12 is folded inwardly back into itself as shown in FIG. 3. The earplug 10 is then inserted into the auditory meatus 24 as shown in FIG. 5. The rings 16 form a seal against the inner surface 26 of the auditory meatus 24. The outer flap 18 additionally helps to seal the plug 10 in the auditory meatus 24.

As can be seen in FIG. 5, a volume of air 28 is defined by the eardrum 30, the interior portion of the inner surface 26 of the auditory meatus, and the closed end 14 of the tubular vessel 12. Water circulates inside of the tubular vessel 12 in the region 32 forcing the vessel walls against the inner surface 26 of the auditory meatus and aiding in the sealing action of the rings 16.

As the diver descends, the ambient water pressure causes the air pressure within the middle ear region 34 to increase. However, the ambient water pressure also exists within the interior 32 of the tubular vessel 12. The increased pressure causes the region 32 to expand and the volume 28 to compress by the flexing or rolling action of the tubular vessel 12 until the closed end 14 is in the position shown by the broken line of FIG. 5. With each doubling of the external ambient water pressure (that is, at depths of 33, 99, and 230 feet) the volume of trapped air between the eardrum 30 and the tubular vessel 12 will decrease by one-half. Normal recreational diving is limited to approximately 100 feet of depth, and the earplug will easily permit the required volume changes.

Since the earplug 10 is molded from a single piece of soft flexible material, the sealing rings 16 will fold upon insertion in a direction which provides a self-energizing seal under a pressure differential. If for some reason the eardrum 30 should rupture, the tubular vessel 12 will unroll and flex to its limit, and then stop. This will prevent the entry of water into the middle ear region 34 and the inner ear regions beyond, not shown, thereby preventing the usual temporary vertigo and subsequent infections.

Although the preferred embodiment utilizes a tubular vessel rolled back upon itself to provide a variable volume of air between the sealing means of the earplug and the eardrum, other means could be employed. For example, longitudinal flutes or pleats could be formed in the body of the tubular vessel 12 to permit a radial expansion of the vessel. Although it is preferred for convenience that the variable volume portion of the earplug be inside the auditory meatus, it is conceivable that for some applications it would be desirable that the variable volume section be placed outside the auditory meatus. Such means could include an external balloon, a ball in a tube, a piston and cylinder combination, or a long open capillary where the volume of the tube passage is much greater than the change in volume of the chamber under pressure and of the volume of the middle and inner ear.

In the disclosed embodiment, the tubular vessel 14 rolls or flexes in response to changes in external pressure. The limit of this flexing is determined when the elastic limit of the vessel material is reached and by the volume of the auditory meatus. This limit and the amount of pressure differential which can be withstood by the vessel 12 can be controlled by the reinforcing means such as the strands 22, as shown in FIG. 1. Other means of achieving control over the limit of flexing include local thickening of the end 14 of the vessel 12, or local hardening of the end 14 by any suitable means.

The disclosed embodiment of the invention is molded from a single piece of elastomer material, with the reinforcing strands 22 cast therewithin. Other types of material could be employed so long as the necessary functional requirements are met. It is desirable that the material be easily flexible to facilitate expansion and contraction of the variable volume with minimal resistance, to provide the greatest ease in pressure equalization. Other requirements of the material include the ability to resist all substances to which a diver may reasonably be expected to be exposed, plus the ability to adequately function in temperature ranges from 32° to approximately 120° F. Furthermore, the material should be sterilizable by boiling, autoclaving, or cleansing with alcohol, detergent, or other agents.

It can be seen that the present invention provides an improved earplug for divers which provides protection of the inner and middle ear regions by excluding water therefrom under all conditions, including the rupture of an eardrum. Furthermore, this is achieved in conjunction with the maintenance of pressure equalization which is necessary as the diver ascends or descends.

What is claimed is:

1. An earplug for the protection of an underwater diver, comprising:

a tubular vessel having a closed inner end, an outer end, and a wall member of freely flexible material having uniform thickness, said vessel being adapted for removable insertion into the auditory meatus; and means connected to said vessel in proximity to said outer end for providing a seal between said vessel and the interior surface of the auditory meatus when said vessel is inserted therein;

said wall member having a first portion lying in proximity to the inner surface of the auditory meatus and a second portion connected to said inner end and folded back so as to be positioned parallel to and radially inward of said first portion such that the interface between said first and second portions is continuously movable over an extended length of said wall member to permit said first portion, said second portion, and said inner end to function as a freely rolling diaphragm in response to changes in the depth of said diver, whereby the volume of the auditory meatus between said sealing means and the tympanic membrane changes from a first volume to a second smaller volume to permit pressure equalization across the tympanic membrane.

2. An earplug as recited in claim 1 wherein said second volume is one half of said first volume or smaller.

3. An earplug as recited in claim 1 wherein said sealing means comprises a plurality of sealing rings surrounding said vessel in proximity to said outer end and seating against an interior surface of the auditory meatus when said earplug is inserted therein.

4. An earplug as recited in claim 3 wherein said sealing means comprises a sealing flap surrounding said outer end and seating upon the exterior entrance of the auditory meatus when said earplug is inserted therein.

5. An earplug as recited in claim 1 wherein said outer end comprises means for allowing the passage of fluid into the interior of said tubular vessel in contact with said inner end on the side thereof opposite the tympanic membrane.

6. An earplug as recited in claim 5 wherein said outer end is unrestricted.

7. An earplug as recited in claim 1 comprising means for limiting the flexibility of said inner end.

8. An earplug as recited in claim 7 wherein said limiting means comprises a local thickening of said inner end.

9. An earplug as recited in claim 7 wherein said limiting means comprises a local hardening of said inner end.

10. An earplug as recited in claim 7 wherein said limiting means comprises a plurality of filaments integrally molded within said vessel.

11. An earplug as recited in claim 10 wherein said filaments extend longitudinally along said vessel and across said inner end.

* * * * *